US00PP28439P3

(12) United States Plant Patent
Braun

(10) Patent No.: US PP28,439 P3
(45) Date of Patent: Sep. 26, 2017

(54) COLUMNAR APPLE TREE NAMED 'A 68-173'

(50) Latin Name: *Malus×domestica*
Varietal Denomination: A 68-173

(71) Applicant: Peter Braun, Geisenheim (DE)

(72) Inventor: Peter Braun, Geisenheim (DE)

( * ) Notice: Subject to any disclaimer, the term of this patent is extended or adjusted under 35 U.S.C. 154(b) by 41 days.

(21) Appl. No.: 14/545,321

(22) Filed: Apr. 22, 2015

(65) Prior Publication Data

US 2016/0316595 P1 Oct. 27, 2016

(51) Int. Cl.
*A01H 5/08* (2006.01)

(52) U.S. Cl.
USPC ..... Plt./175

(58) Field of Classification Search
USPC ..... Plt./175
See application file for complete search history.

*Primary Examiner* — Keith Robinson
(74) *Attorney, Agent, or Firm* — The Webb Law Firm

(57) ABSTRACT

A new and distinct apple tree variety is provided which exhibits a columnar tree type. The fruit has a very juicy flesh with a good sweet/sour balance, providing a desirable dessert apple.

5 Drawing Sheets

Botanical classification: *Malus×domestica.*
Varietal denomination: 'A 68-173'.

BACKGROUND OF THE INVENTION

The present invention comprises a new and distinct cultivar of *Malus×domestica* apple tree known by the varietal name 'A 68-173'. The new variety was bred in Geisenheim, Germany and is result of the sexual recombination of *Malus×domestica* 'Pinova' (male parent, U.S. Plant Pat. No. 11,601) with *Malus×domestica* 'Waltz' (female parent, unpatented). 'A 68-173' was then asexually reproduced by budding.

When compared to 'Pinova', 'A 68-173' exhibits a more compact growth habit and is more bushy with longer basal side shoots that first grow outward and then vertically upright. The fruit of 'A 68-173' is flatter in shape than the fruit of 'Pinova' with less red color. 'A 68-173' is similar to 'Pinova' in its tolerance against mildew and apple scab.

When compared to 'Waltz', 'A 68-173' exhibits a more open growth habit, longer internodes, thinner and longer side shoots, higher tolerance against mildew and apple scab, no known susceptibility against apple canker, no alternate bearing habit, and the fruits of 'A 68-173' are much firmer with a far superior eating quality.

Further, when compared to apple tree variety named 'ROSALIE' (U.S. Plant Pat. No. 25,501), the new variety is similar to 'ROSALIE' in exhibiting a columnar and diploid tree type. However, 'A 68-173' produces heavier (average of 227 grams or greater versus 61 grams) and larger-sized fruits than 'ROSALIE' with a far superior eating quality. Also, the fruit flesh of 'A 68-173' is 155A, while the fruit flesh of 'ROSALIE' is partly 51A and partly 158D.

The following characteristics distinguish the new variety from other varieties known to the breeder:

Vigorous, columnar tree type;
Good drought tolerance;
Diploid tree type that responds to any mid-season pollinators; and
Tolerance to mildew and apple scab.

The new variety has been trial and field tested and has been found to retain its distinctive characteristics and remain true to type through successive asexual propagations.

DESCRIPTION OF THE DRAWINGS

The accompanying photographic drawings illustrate the new cultivar at seven years of age, with the color being as nearly true as is possible with color illustrations of this type. It should be noted that colors may vary with growing conditions and time of year.

DESCRIPTION OF THE PLANT

Figure 1:
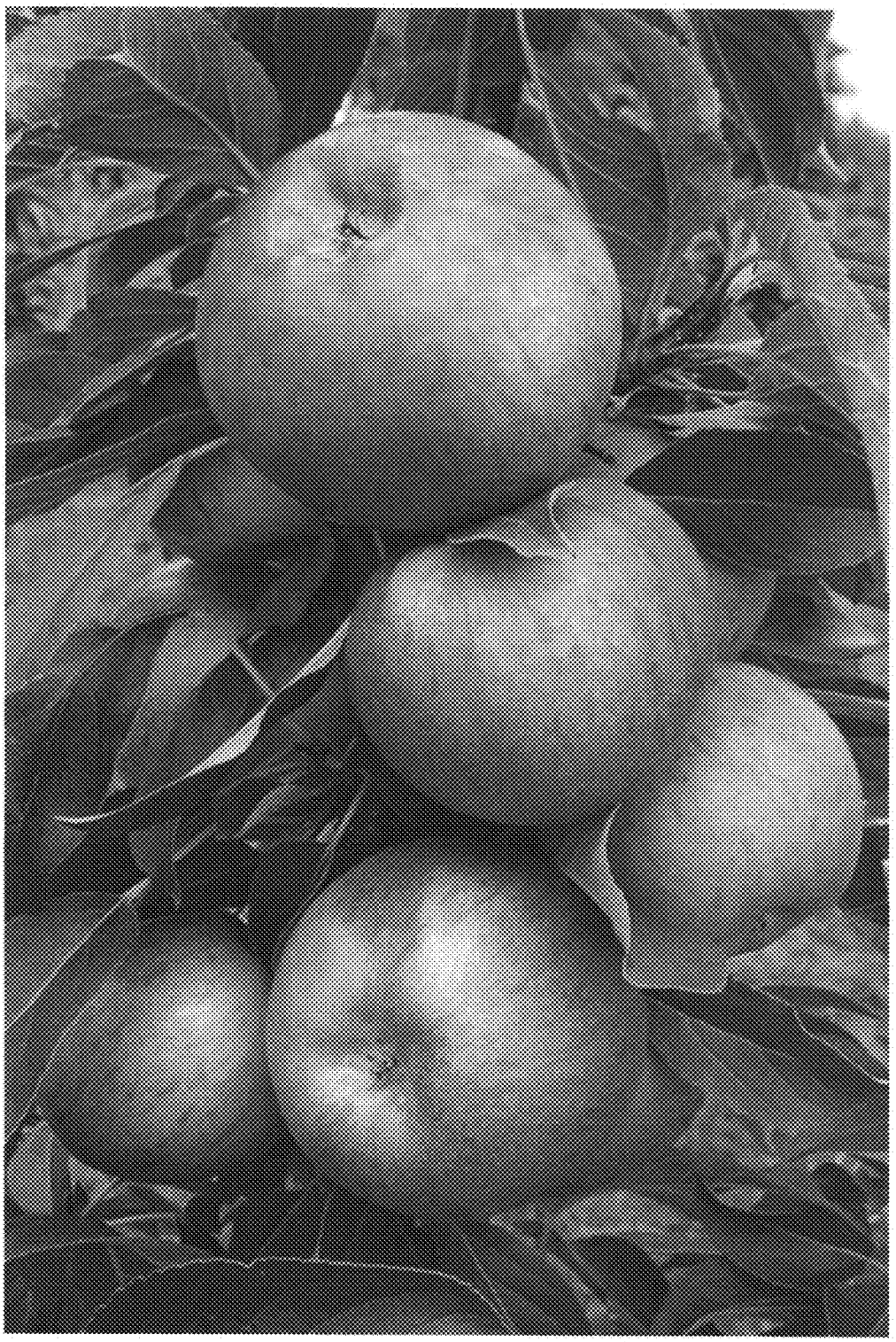
FIG. 1 shows a close-up view of the fruits of the new variety.
Figure 2:
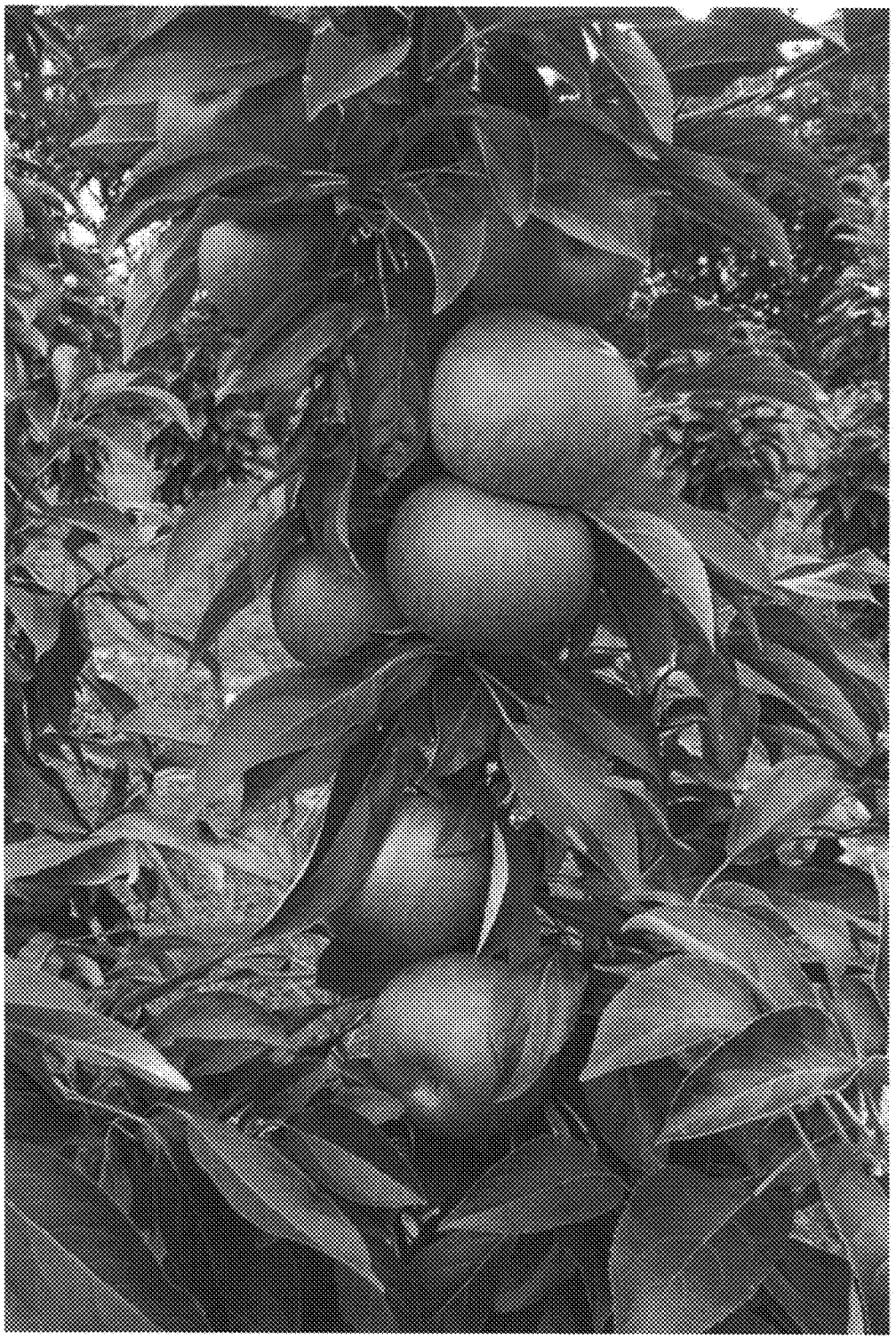
FIG. 2 shows a close-up view of the fruits of the new variety.
Figure 3:
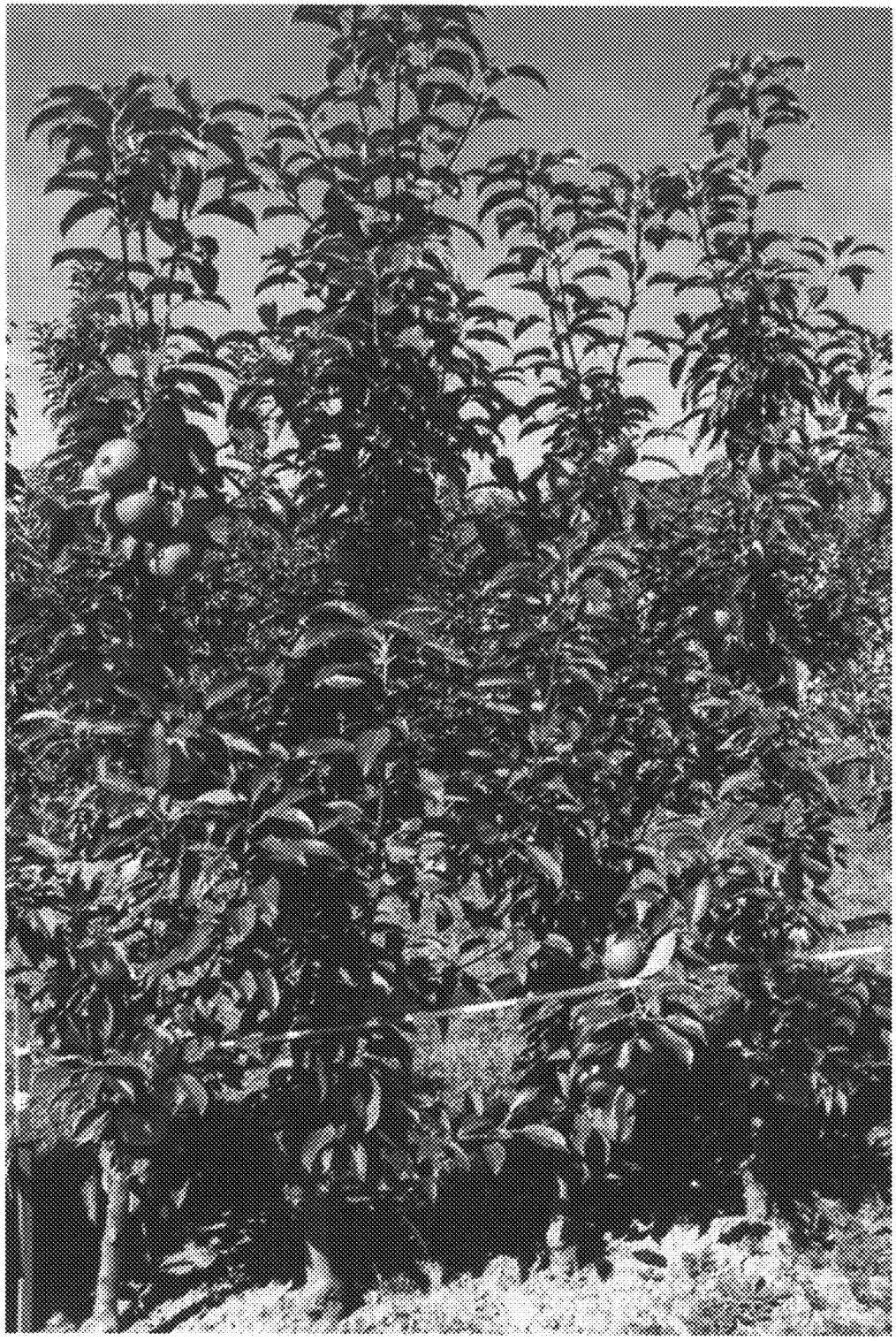
FIG. 3 is a photograph of multiple trees of the new variety.
Figure 4:
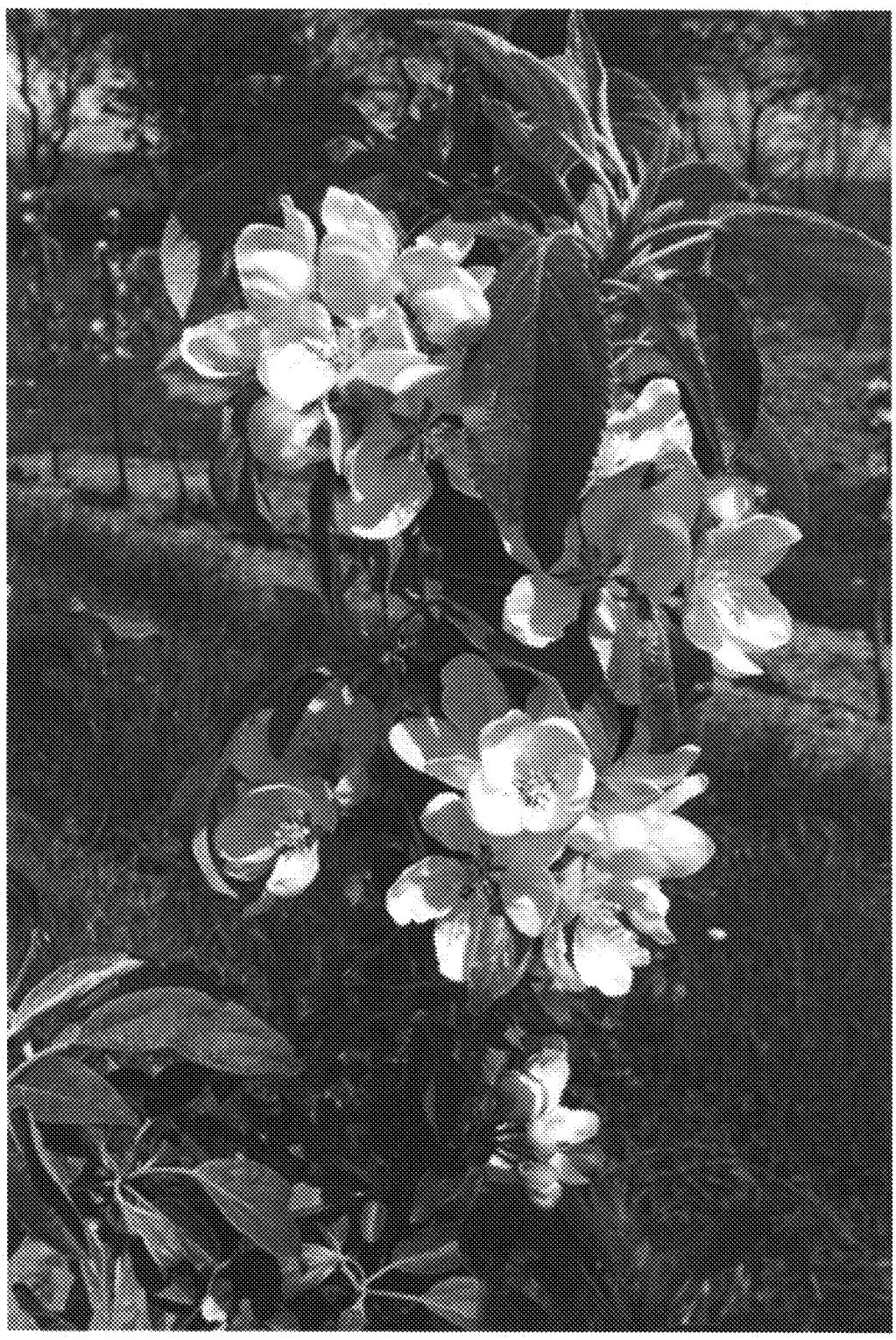
FIG. 4 shows the blossoms and leaves of the new variety.
Figure 5:
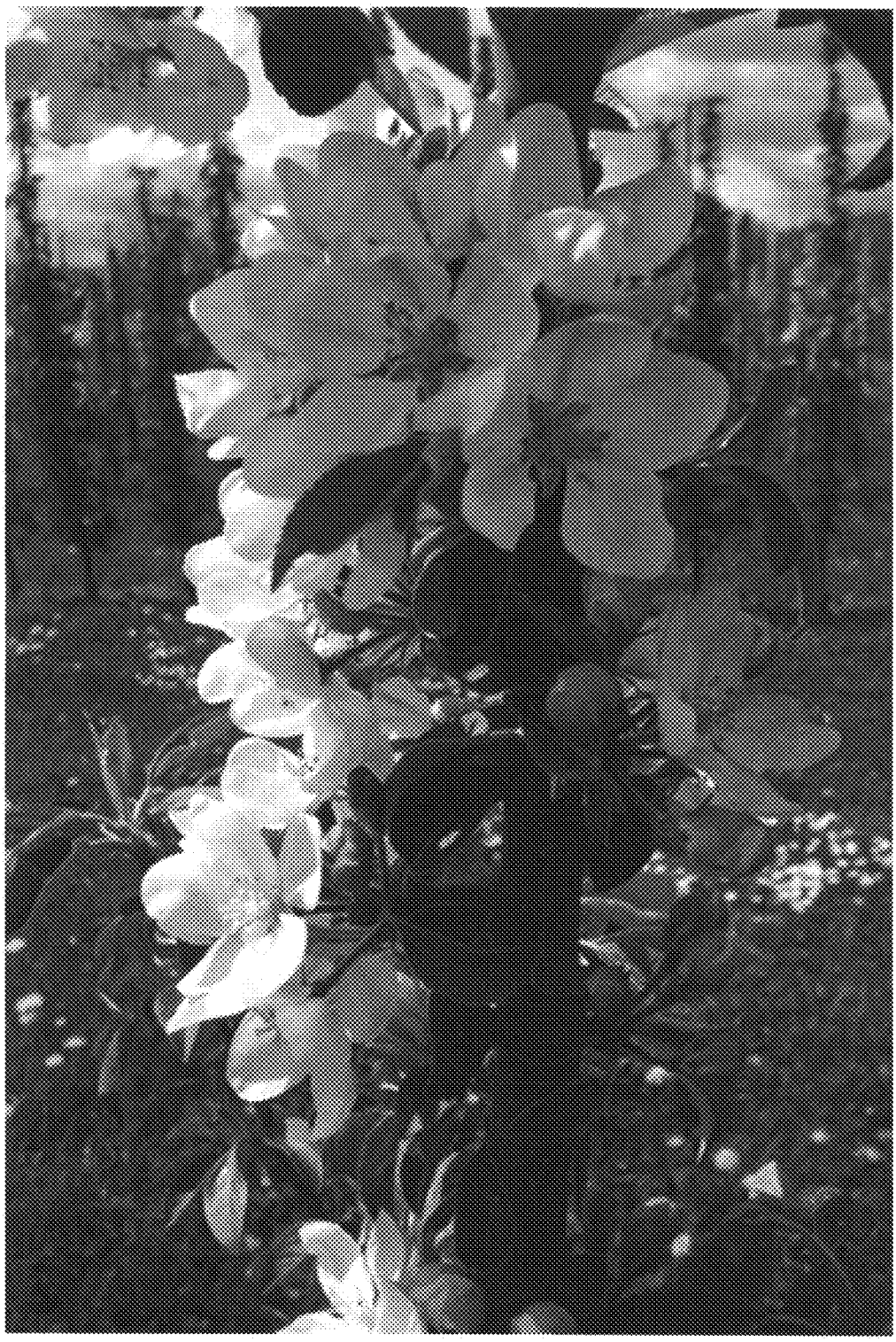
FIG. 5 shows the blossoms of the new variety.

The following detailed description sets forth the characteristics of the new cultivar collected at seven years of age. The new variety was grown under natural field conditions in Oregon. Color references are primarily to The 2015 R.H.S. Colour Chart of The Royal Horticultural Society of London and were identified under natural light.

TREE

Internode length of one-year old shoot: Approximately 25 mm.

Leaf blade:

*Attitude in relation to shoot.*—Upwards.
*Length.*—70-90 mm.
*Width.*—Approximately 42 mm.
*Color.*—140B (upper surface); 144C (lower surface).

*Texture*.—Smooth (upper surface); smooth with light pubescence present (lower surface).

Petiole:

*Length*.—22 mm.

*Color*.—144C.

*Texture*.—Smooth.

Flower:

*Time to beginning of flowering*.—Midseason; around early April in Dundee, Oreg.

*Depth*.—Approximately 6 mm.

*Width*.—Approximately 8 mm.

*Petal arrangement*.—Five overlapping petals.

*Petal color*.—155B to 56C for an open flower.

Fruit:

*Bearing*.—Annual without alternate bearing.

*Maturity when described*.—Eating maturity — after 2 months in common storage.

*Date of picking*.—Sep. 20, 2013.

*Weight*.—Average of 227 grams or more per fruit, even with large crop loads.

*Size*.—Axial diameter: Average of 7 cm. Transverse diameter: Average of 9 cm.

*Form*.—Slightly flattened.

*Cavity*.—Shape: Funnel-shaped, slightly Russet. Depth: 27 mm. Breadth: 18 mm. Stalk cavity: Depth is approximately 41 mm and width is approximately 2 mm.

*Basin*.—Shape: Shallow/wide, with irregularities. Depth: 10 mm. Width: 17 mm. Eye basin: Depth is approximately 20 mm and width is approximately 45 mm.

*Calyx*.—Irregular, with some bumps.

*Flavor*.—Sweet and tart; very intense.

*Sugar average*.—15 brix.

Skin:

*Thickness*.—Medium.

*Texture*.—Firm and juicy.

*Tendency to crack*.—Absent.

*Color*.—Bicolored; 40% red 42A color with a green background.

*Ground color*.—144B.

*Bloom*.—Absent.

*Over color*.—Small to medium area of red 50A over color (30-50%), which is less than 'Pinova'. The intensity is medium with very strong striping.

*Russet*.—Absent around the stalk attachment and eye basin of the fruit.

Flesh:

*Aroma*.—Slight.

*Color*.—White; 155A.

*Texture*.—Fine, with some dents.

*Eating quality*.—Very juicy with a combined tart/sweet flavor.

*Firmness*.—Firm to about 17 pounds of pressure. The fruit holds firmness for 3 weeks on the tree and loses firmness during storage.

Core:

*Bundle area*.—35 mm in size, with tight seed carpels.

*Bundle*.—Lightly defined vascular strands.

*Calyx tube*.—Narrow and funnel-shaped.

*Depth of tube to shoulder*.—14 mm; calyx tube itself is about 7 mm long.

*Styles*.—Persistent as dry residues.

*Stamens*.—Persistent as dry residues.

*Seed cells*.—Wall: Smooth. Depth: 10 mm. Breadth: 5 mm. Longitudinal section: 9 mm.

Seeds:

*Number perfect*.—10.

*Number in one cell*.—2.

*Length*.—10 mm.

*Breadth*.—5 mm.

*Form*.—Oval.

*Color*.—177B.

Stem:

*Length*.—15 mm.

*Width*.—3 mm on average.

*Color*.—191A.

Reproductive organs:

*Average pistil number per flower*.—1.

*Stigma shape*.—Bulbous.

*Anthers*.—Arranged in a single line around the pistil with a color of 9C.

Pollen amount: Moderate.

Use: High quality, dessert variety for fresh consumption.

Keeping quality: Moderate, can be stored for 12 weeks and hold firmness. Harvesting lasts for 4 weeks.

Drought tolerance: Good.

Disease resistance: Tolerant to mildew (*Podosphaera leucotricha*) and apple scab (*Venturia inaequalis*). The leaves are clean of fungus without using antifungal spray.

I claim:

1. A new and distinct variety of columnar apple tree substantially as is herein described and illustrated.

* * * * *